United States Patent [19]

Klass

[11] 4,057,575

[45] Nov. 8, 1977

[54] PROCESS FOR THE PREPARATION OF UNSATURATED ESTERS

[75] Inventor: Donald L. Klass, Barrington, Ill.

[73] Assignee: Union Oil Company of California, Brea, Calif.

[21] Appl. No.: 699,198

[22] Filed: June 23, 1976

Related U.S. Application Data

[63] Continuation of Ser. No. 670,159, Sept. 25, 1967, abandoned, which is a continuation-in-part of Ser. No. 141,832, Sept. 29, 1961.

[51] Int. Cl.$^2$ ............................................. C07C 67/05
[52] U.S. Cl. .................................. 560/245; 560/113; 560/81; 260/604 AC; 260/614 AA; 260/615 AA; 560/243; 560/71; 560/105; 560/95; 560/64; 260/410.9 N
[58] Field of Search ............ 260/497 A, 475 N, 476 R

[56] References Cited

U.S. PATENT DOCUMENTS

| | | | |
|---|---|---|---|
| 2,065,540 | 12/1936 | Schneider | 260/614 |
| 2,764,610 | 9/1956 | Kuder | 260/497 |
| 2,858,331 | 10/1958 | Feske et al. | 260/497 |
| 2,962,534 | 11/1960 | Montagna et al. | 260/614 |
| 3,021,373 | 2/1962 | Montagna et al. | 260/614 |
| 3,190,912 | 6/1965 | Robinson | 260/497 |
| 3,275,680 | 9/1966 | Holzrichter et al. | 260/497 |
| 3,300,528 | 1/1967 | Wakasa | 260/497 |
| 3,373,189 | 3/1968 | Lum | 260/497 |
| 3,479,392 | 11/1969 | Stern et al. | 260/497 |
| 3,658,888 | 4/1972 | Hornig et al. | 260/497 |

FOREIGN PATENT DOCUMENTS

| | | | |
|---|---|---|---|
| 638,489 | 2/1964 | Belgium | 260/497 |
| 648,814 | 12/1964 | Belgium | 260/497 |
| 1,407,526 | 6/1965 | France | 260/497 |
| 1,426,776 | 12/1965 | France | 260/497 |
| 137,511 | 4/1960 | U.S.S.R. | 260/497 |

OTHER PUBLICATIONS

Moiseev et al., Doklady Akademii Nawk, SSSR, 130, pp. 820–823 (1960).
Smidt, Chemistry and Industry, pp. 54–61, (1/13/62).
Moiseev et al., Doklady Akademii Nawk, SSSR, 133, pp. 801–804 (1960).
Berkman, Catalysis, pp. 458–463 (1960).
USP 3,850,980, 11–1974, Clark et al., 260/497

Primary Examiner—James O. Thomas, Jr.
Assistant Examiner—Michael Shippen
Attorney, Agent, or Firm—Richard C. Hartman; Dean Sandford; Michael H. Laird

[57] ABSTRACT

The invention comprises the oxidation of olefins to unsaturated esters of organic acids or acetals and/or unsaturated ethers of alcohols by contacting the olefin with an organic acid or alcohol reactant in the presence of a catalyst comprising a compound of a Group VIII noble metal and a redox agent. The catalyst is maintained active by contacting it with oxygen introduced simultaneously or intermittently with the olefin or by circulating the catalyst between separate oxygen and olefin contacting zones. The oxidation can be performed under liquid phase conditions by initiating the contacting with a dissolved catalyst or can be performed under vapor phase conditions by initiating the contacting with the catalyst distended on a solid support.

11 Claims, No Drawings

PROCESS FOR THE PREPARATION OF UNSATURATED ESTERS

DESCRIPTION OF THE INVENTION

This application is a continuation of my application Ser. No. 670,159, filed Sept. 25, 1967 now abandoned, which was a continuation-in-part of Ser. No. 141,832, filed Sept. 29, 1961.

This invention relates to a process for the synthesis of vinyl ethers and vinyl esters. More particularly, this invention relates to a process for the synthesis of vinyl ethers and vinyl esters from olefins and alcohols or carboxylic acids.

In accordance with this invention, vinyl esters are prepared by contacting a mixture of an olefin and a carboxylic acid with a catalyst system consisting of a compound of a noble metal from Group VIII of the Periodic Table and a regenerative oxidant capable of keeping the noble metal in oxidized form. Vinyl ethers are prepared by contacting a mixture of an olefin and an alcohol with the same type of catalyst system. The oxidant may be continuously regenerated in place by introducing an oxygen-containing gas into the reaction zone, or it may be regenerated by periodically or continuously withdrawing the catalyst system from the reaction zone, contacting it with oxygen-containing gas, and returning it to the reaction zone.

It becomes therefore a primary object of this invention to provide a process for preparing vinyl esters and vinyl ethers.

An object of this invention is to provide a process for the synthesis of vinyl ethers by reaction of olefins and alcohols.

An object of this invention is to provide a process for the synthesis of vinyl esters by reaction of olefins and acids.

An object of this invention is the provision of a process for producing vinyl ethers by the reaction of olefins and alcohols in the presence of a catalyst system consisting of a compound of a noble metal from Group VIII of the Periodic Table and a regenerative oxidant capable of keeping the noble metal in oxidized form.

The drawing is a flow diagram of one embodiment of this invention.

The process of this invention is conducted by maintaining the catalyst system in solution or suspension in the alcohol or acid and passing the olefin, in vapor form, through the liquid suspension. An alternative mode for carrying out the invention comprises supporting the catalyst system on an inert, particulate solid and passing a vaporized mixture of olefin and acid or alcohol through the bed of solid.

The olefinic reactants used in accordance with this invention may be any olefinic or diolefinic hydrocarbon. Suitable olefinic hydrocarbons are ethylene, propylene, alpha-butylene, beta-butylene, pentene and its homologs, cyclohexene and styrene. Mixtures of olefins, or gases containing olefins or other unsaturated compounds, may be used in the reaction of this invention provided they are capable of reacting under the reaction conditions. The reaction of olefins containing two to three carbon atoms constitutes a preferred group of starting materials. Under certain reaction conditions, it may be necessary to adjust the temperature and pressure so that the reaction will go forward with particular olefins, taking into account their physical properties. Where higher olefins are used, the products will have correspondingly higher boiling points which may also require corresponding modifications in the reaction conditions.

The alcohols used in accordance with this invention may comprise any primary, secondary, or tertiary alcohol containing 1 to 20 carbon atoms. Examples of alcohols coming within this formula are methyl, ethyl, propyl, isopropyl, butyl, isobutyl, t-butyl, amyl, isoamyl, neopentyl, hexyl, isohexyl, heptyl, octyl, nonyl, decyl, undecyl, dodecyl, tridecyl, tetradecyl, pentadecyl, hexadecyl, heptadecyl, octadecyl, nonadecyl, and eicosyl alcohol. Other alcohols that can be used include pentane-2, methylisopropyl carbinol, t-amyl alcohol, 2-methylpentanol-1, 3-methylpentanol-1, t-amyl carbinol, 2-ethylbutanol-1, neopentyl carbinol, 2,3-dimethylbutanol-1, hexanol-2, hexanol-2,3-methylpentanol-2, methylisobutyl carbinol, ethylisopropyl carbinol, pinacolyl alcohol, 2-methylpentanol-2, methyldiethyl carbinol, dimethylisopropyl carbinol, diisopropyl carbinol, 2,4-dimethylpentanol-1, pentamethylethanol, capryl alcohol, lauryl alcohol, pentadecanol-1, cetyl alcohol, carnaubyl alcohol, aryl alcohol, montanyl alcohol, ginnol, melissyl alcohol, myricyl alcohol, gossypyl alcohol, lacceryl alcohol, and psyllicyl alcohol.

The acids used in accordance with this invention have the formula $R'(COOH)_m$, wherein $R'$ is any hydrocarbon radical having 1 to 20 carbon atoms and $m$ has the value of 1 to 5.

Where $R'$ is an aliphatic radical, the following acids are intended:
acetic acid
propionic acid
n-butyric acid
isobutyric acid
n-valeric acid
trimethyl acetic acid
caproic acid
n-heptylic acid
caprylic acid
pelargonic acid Where $R'$ is an aromatic radical, an alkylaryl radical, an aralkyl radical or the like, the following acids are contemplated: benzoic, o-toluic, m-toluic, p-toluic, salicylic, anisic, phthalic, terephthalic, hemimellitic, trimellitic, trimesic, prehnitic, phenyacetic, hydrocinnamic, γ-phenylbutyric, δ-phenyl-n-valeric, ε-phenyl-n-caproic, homophthalic, o-phenylene diacetic, m-phenylene-diacetic, p-phenylene diacetic and o-phenyleneacetic-β-propionic acid.

Alkali and alkaline earth metal salts of these acids in mixtures with the acids may also be used. Thus the reaction can be carried out using sodium acetate, calcium acetate, potassium propionate, barium isobutyrate, calcium acetate, magnesium acetate, magnesium butyrate, sodium valerate, lithium trimethylacetate, barium caproate, calcium palmitate, sodium laurate, calcium caproate, and the like as part of the acid-producing ingredients.

Examples of $R'$ groups coming within the foregoing definition are methyl, ethyl, propyl, isopropyl, butyl, isobutyl, t-butyl, amyl, isoamyl, hexyl, isohexyl, heptyl, octyl, nonyl, decyl, undecyl, dodecyl, tridecyl, tetradecyl, pentadecyl, hexadecyl, heptadecyl, octadecyl, nonadecyl, and eicosyl groups. Other acids that can be used include isovaleric, methylethylacetic, isocaproic, methyl-n-propylacetic, diethylacetic, sec-butylacetic, dimethylethylacetic, tert-butylacetic, methyl-isopropylacetic, methyl-t-butylneopentylacetic, myristic, palmitic, margaric, and dicetylacetic acid.

If a mixture of carboxylic acid and salt is used, such as $RCO_2H$ and $RCO_2Na$, the salt can be preformed by pretreating the acid feed to the reactor with sodium hydroxide, for example, or the salt can be added directly to the reactor.

The catalyst for the reaction comprises compounds of the noble metals of Group VIII of the Periodic Table, including compounds of palladium, iridium, osmium, ruthenium, rhodium and platinum. Specific examples are platinum and palladium chlorides.

The reduction-oxidation system that is used to continuously maintain the catalyst in its oxidized form is brought about by compounds of metals which, under the reaction conditions, may be present in various oxidation stages. Examples are compounds of copper, mercury, lead, cerium, thallium, tin, titanium, vanadium, antimony, chromium, molybdenum, uranium, manganese nickel, iron and cobalt. Examples of suitable regenerative oxidants capable of maintaining the noble metal in oxidized form are cupric chloride, cupric bromide, cupric iodide, cupric acetate, cupric nitrate, cupric sulfate, mercuric acetate, mercuric bromate, mercuric bromide, mercuric iodide, mercuric carbonate, mercuric chloride, chromic bromide, chromic chloride, nickel chloride, nickel bromide, nickel iodide, ferric chloride and cobalt chloride. Other redox systems include iodide/iodine systems, arsenite/arsenate, sulfite/sulfate systems, or organic redox systems including oxobenzene/hydrazobenzene, or quinones or hydroquinones of the benzene, anthracene or phenanthrene series.

The reaction may be carried out in a medium containing an active oxidizer, or in the presence of an active oxidizer such as oxygen, ozone, peroxidic compounds (especially hydrogen peroxide), oxides of nitrogen, free halogens, halogen-oxygen compounds, or compounds of the higher valence stages of metals such as manganese, cerium, chromium, selenium, lead, vanadium, silver, molybdenum, cobalt and osmium. The presence of the active oxidizer promotes the reformation of the higher oxidation stage of the active catalyst component which is necessary for the promotion of the reaction. Some of these oxidizing agents may be produced during the reaction. In some instances it may be advantageous to add an oxidizing agent to the reaction as it proceeds. In general, any of the catalyst-oxidant systems used in the so-called Consortium process are suitable for use in the process of this invention. One of the most practical catalystoxidant systems is the combination of palladium chloride, anhydrous hydrogen chloride and cupric chloride. Using this catalyst combination as an illustration, the various combinations of reactants and catalyst systems that are contemplated by this invention may be represented as follows:

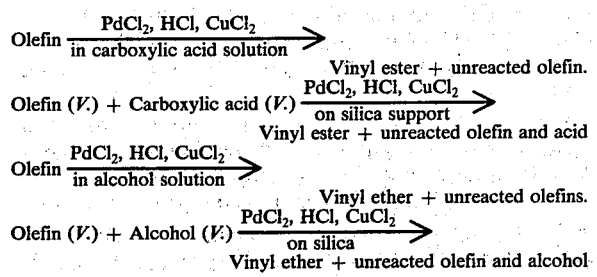

In all of the foregoing reactions, the feedstocks must be substantially anhydrous in order to avoid the formation of aldehydes and ketones, but this invention may also be used for the continuous and cyclic preparation of aldehydes and ketones by subjecting the vinyl ether or ester in the product stream to hydrolysis with water, preferably acidic water. The carbonyl compound is liberated along with the starting alcohol or acid. The unreacted oxygen, olefin and liberated acid or alcohol are recycled to the reactor and the carbonyl compound is scrubbed out, distilled, or extracted, depending on its nature.

For example, with ethylene and an alcohol, referring to the drawing, the feed mixture enters line 10 and reactor 12 wherein the catalyst, comprising a noble metal halide, haloacid and heavy metal halide in alcohol solution, is maintained. The reaction produces a product mixture containing unreacted ethylene, vinyl ether and unused oxygen, which is sent via line 14 to hydrolysis reactor 16. As the result of the hydrolysis, a water solution of acetaldehyde is drawn off at line 18 and an overhead comprising unused oxygen, ethylene and alcohol (which is preferably water-insoluble) is taken off at line 20, sent to dryer 22 and recycled via line 24. The reaction can be carried out in an alcohol or acid carrier-reactant and any make-up acid or alcohol is added at line 26.

This process has the advantage that the reactor can be maintained at any desired temperature, at atmospheric pressure, by proper selection of the alcohol or acid without distillation occurring. For example, when propionic acid is used, the temperature of the reactor can be maintained up to the boiling point of propionic acid. It is, of course, preferable that the acid or alcohol used be insoluble in water and that the carbonyl compound liberated be soluble in water so that the aldehyde or ketone can be easily scrubbed out in the hydrolysis unit, but this is not a limitation. Other methods can be used to separate the carbonyl compound.

In order to illustrate the invention, the following examples are given:

EXAMPLE 1

Ethylene in vapor form is passed through a reservoir of liquid acetic acid to vaporize a preselected amount of the acid, and the resulting mixture is passed through a bed of catalyst consisting of palladium chloride ($PdCl_2$), hydrogen chloride, and cupric chloride ($CuCl_2$) supported on silica. The vinyl acetate is removed as product from the effluent gas stream, and the unreacted ethylene is recycled to the reactor. The flow of ethylene and acetic acid to the reactor is interrupted periodically, and a stream of oxygen is passed through the catalyst bed to regenerate the oxidant.

EXAMPLE 2

Ethylene in vapor form is passed through a reservoir of liquid acetic acid to vaporize a preselected amount of the acid, a small amount of air is added continuously to the resulting gas mixture, and the mixture is passed through a bed of catalyst consisting of palladium chloride, anhydrous hydrogen chloride, cupric chloride and sodium acetate supported on one-eighth inch silica pellets.

The reservoir of liquid acetic acid is contained in a three-necked, round-bottom, one-liter flask which is maintained at 107°–110° C. fitted with a thermowell, stirrer and exit tube leading to the reactor containing the catalyst. The reactor comprises a U-shaped tube about 12 millimeters in diameter packed with the catalyst and the tube is immersed in a constant temperature bath comprising a reservoir of acetic acid maintained at its reflux temperature of 118° C.

The catalyst is prepared by mixing 16 grams of one-eighth inch silica pellets with 8 milliliters of an aqueous solution containing 15.3 weight percent hydrogen chloride, 7.8 weight percent cupric chloride, 5.8 weight percent palladium chloride and 18.9 weight percent sodium acetate. The pellets are then dried at 170° C. for 45 minutes and placed in the reaction tube.

The vinyl acetate is removed as a product from the effluent gas stream by connecting the exit end of the reactor to a product trapping system consisting of a gas bubbler filled with acetic acid and a cold trap condenser cooled by an isopropyl alcohol-dry ice trap.

The experiment is performed by introducing ethylene at a flow rate of 2.73 cubic feet per hour and air at 0.312 cubic feet per hour to provide about ten parts air per ninety parts of ethylene.

The oxidation is performed in a series of experiments of successively increasing durations and at the end of each experiment the product traps are replaced with fresh traps and the reactor is replaced with an identical reactor containing a freshly prepared catalyst. The removed product traps are sampled and the samples analyzed by vapor phase chromatography to determine the yields of product. The catalyst is emptied from the removed reactor and analyzed for its metallic and ionic palladium content. In this analysis, separate samples of the catalyst are analyzed by a standardized polarographic procedure to determine the amount of soluble or ionic palladium in one sample and the total amount of palladium (after dissolution of the solid in hydrofluoric acid) in the second sample.

The yields of vinyl acetate and acetaldehyde and the composition of the catalyst at the end of each experiment are reported in the following Table:

Table 1

| Experiment | Reaction Time (Hr.) | Products (Grams) | | Percent palladium as: | |
|---|---|---|---|---|---|
| | | Acetaldehyde | Vinyl Acetate | Pd° | Pd++ |
| 1 | 3 | 0.000140 | 0.0 | 31.5% | 68.5% |
| 2 | 5 | 0.000245 | 0.000720 | 42.9 | 57.1 |
| 3 | 8.5 | 0.083000 | 0.026800 | 47.2 | 52.8 |
| 4 | 10.5 | 0.062900 | 0.000265 | 49.6 | 50.4 |

EXAMPLE 3

Ethylene in vapor form is passed through a reservoir of liquid ethanol to vaporize a preselected amount of the alcohol, and the resulting mixture is passed through a bed of catalyst consisting of palladium chloride (PdCl$_2$), hydrogen chloride, and cupric chloride (CuCl$_2$) supported on silica pellets. The vinyl ethyl ether is removed from the reactor effluent and the unreacted ethylene and ethanol are recycled to the reaction zone.

EXAMPLE 4

Ethylene is passed through an anhydrous acetic acid solution of palladium chloride, hydrogen chloride and cupric chloride. The resulting vinyl acetate is recovered from the reactor effluent stream and the unreacted ethylene is recycled. After a few hours of operation, the introduction of ethylene is interrupted and a stream of dilute oxygen in nitrogen is passed through the acetic acid solution to regenerate the oxidant portion of the catalyst system.

EXAMPLE 5

Ethylene containing a small amount of air is bubbled through an anhydrous acetic acid solution of sodium acetate, palladium chloride, hydrogen chloride and cupric chloride. The catalyst solution is prepared by adding an anhydrous solution of 4 grams of hydrochloric acid in 36 grams acetic acid, 2 grams cupric chloride, 1.5 grams palladous chloride and 6 grams sodium acetate to 500 grams glacial acetic acid.

The solution is contained in a one-liter, round-bottom, three-necked flask equipped with a mechanical stirrer, gas inlet tube for introducing the ethylene and air mixture into the solution, a thermowell, a rubber stopple outlet, and a gas exit tube leading to a product trapping system consisting of a gas bubbler filled with acetic acid and a cold trap condenser cooled by an isopropyl alcohol-dry ice trap. The resulting vinyl acetate is recovered from the reactor effluent stream in the product trapping system.

The thermowell is fitted with a thermometer to monitor the temperature and the reaction flask is heated with a heating mantle controlled by a Variac regulator to maintain the flask contents up to the boiling point of acetic acid, at 108°–100° C. The rubber stopple outlet is maintained closed and is used to admit a syringe to periodically withdraw a sample of the catalyst solution.

Ethylene and air are admitted to the reaction flask through individual rotometers and valves set to control the rate of flow of these gases. Separate experiments are performed using varied amounts of air relative to the amount of ethylene charged to the catalyst solution. The small amount of oxygen in the air maintains the oxidant of the catalyst system in the active form, permitting continuous operation of the reaction for a prolonged period of time.

Each experiment is performed for a reaction period of 20–21 hours and at each 3½ to 4 hour interval during the reaction period the trapping system is removed and replaced with a fresh system and the contents of the removed traps are immediately weighed and sampled and the samples are injected into a gas-liquid chromatograph and analyzed to determine the total amount of product. At the time that the trapping system is changed, a sample of the flask liquid contents is withdrawn with a syringe and transferred under nitrogen to a sample bottle.

The liquid in the sample bottle is analyzed with a standard polarographic procedure to determine the amount of cuprous, cupric and palladous ions present. A separate portion of the liquid sample is evaporated to a residue, the residue is oxidized with nitric, nitric-perchloric and sulfuric-perchloric acids in successive treatments, then dissolved in mixed nitric and hydrochloric acids and then analyzed by the polarographic procedure to determine the total copper and palladium present.

The following Table summarizes the results when the air comprises 10 percent of the ethylene-air mixture:

Table 2

| Reaction Time (Hr.) | Vinyl Acetate (Gm.) | Acetaldehyde (Gm.) | Ratio Pd°/Pd++ | Ratio Cu+/Cu++ |
| --- | --- | --- | --- | --- |
| 3.5 | 0.002 | 0.200 | 0.085 | 2.1 |
| 6.5 | 0.0417 | 0.114 | 0.098 | 1.9 |
| 10.5 | 0.149 | 0.102 | 0.313 | 2.6 |
| 13.5 | 0.097 | 0.018 | 0.632 | 1.3 |
| 17.5 | 0.150 | 0.007 | 1.00 | 0.0 |
| 20.5 | 0.091 | 0.001 | 6.63 | 0.2 |

The following Table summarizes the results when the air comprises 20 percent of the ethylene-air mixture:

Table 3

| Reaction Time (Hr.) | Vinyl Acetate (Gm.) | Acetaldehyde (Gm.) | Ratio Pd°/Pd++ | Ratio Cu+/Cu++ |
| --- | --- | --- | --- | --- |
| 4.0 | 0.016 | 0.024 | 0.056 | 3.0 |
| 7.0 | 0.052 | 0.130 | 0.048 | 0.19 |
| 11.0 | 0.102 | 0.146 | 0.063 | 0.57 |
| 14.0 | 0.064 | 0.038 | 0.257 | 0.34 |
| 17.5 | 0.152 | 0.081 | 0.620 | 0.44 |
| 20.5 | 0.118 | 0.019 | 0.620 | 1.7 |

The following Table summarizes the results when the air comprises 30 percent of the ethylene-air mixture:

Table 4

| Reaction Time (Hr.) | Vinyl Acetate (Gm.) | Acetaldehyde (Gm.) | Ratio Pd°/Pd++ | Ratio Cu++/Cu+ |
| --- | --- | --- | --- | --- |
| 4.0 | 0.0 | 0.262 | 0.115 | 0.575 |
| 7.0 | 0.020 | 0.171 | 0.313 | 0.0 |
| 11.0 | 0.080 | 0.175 | 0.378 | 0.487 |
| 14.0 | 0.176 | 0.069 | 0.532 | 0.450 |
| 18.5 | 0.108 | 0.071 | 0.360 | 0.054 |
| 21.5 | 0.103 | 0.024 | 0.516 | 0.0 |

The following Table summarizes the results when the air comprises 40 percent of the ethylene-air mixture:

Table 5

| Reaction Time (Hr.) | Vinyl Acetate (Gm.) | Acetaldehyde (Gm.) | Ratio Pd°/Pd++ | Ratio Cu+/Cu++ |
| --- | --- | --- | --- | --- |
| 3.5 | 0.0 | 0.251 | 0.028 | 0.895 |
| 6.5 | 0.028 | 0.203 | 0.094 | 0.368 |
| 10.5 | 0.037 | 0.245 | 0.141 | 0.698 |
| 13.5 | 0.075 | 0.137 | 0.163 | 0.462 |
| 17.5 | 0.097 | 0.142 | 0.119 | 0.218 |
| 20.5 | 0.095 | 0.042 | 0.275 | 0.184 |

The following Table summarizes the results when the air comprises 50 percent of the ethylene-air mixture:

Table 6

| Reaction Time (Hr.) | Vinyl Acetate (Gm.) | Acetaldehyde (Gm.) | Ratio Pd°/Pd++ | Ratio Cu+/Cu++ |
| --- | --- | --- | --- | --- |
| 4.5 | 0.011 | 0.363 | 0.027 | 0.422 |
| 7.0 | 0.031 | 0.200 | 0.119 | 0.326 |
| 10.0 | 0.051 | 0.311 | 0.096 | 0.846 |
| 13.0 | 0.044 | 0.134 | 0.045 | 0.177 |
| 17.0 | 0.136 | 0.208 | 0.218 | 0.822 |
| 20.0 | 0.110 | 0.079 | 0.132 | 0.488 |

In some cases, the reaction of the olefin and the alcohol tends to give mixtures of acetals and vinyl ether, or acetals alone. In these cases, the product gases are passed over catalysts which are known to eliminate alcohol from the acetal to give the vinyl ether.

Thus:

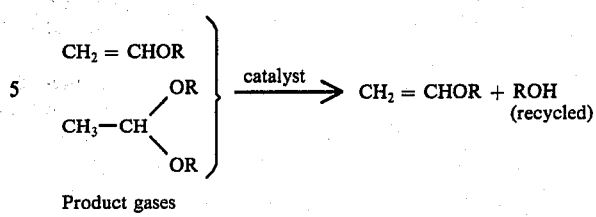

Product gases

Similar processes may be used with the product streams with acids which may contain alkylidene diacetates, for example, when acetic acid is used.

EXAMPLE 6

Ethylene is passed through an ethanolic solution of palladium chloride, hydrogen chloride, and cupric chloride. The resulting mixture of vinyl ethyl ether and diethyl acetal is removed from the reactor effluent stream and the unreacted ethylene is recycled. The product mixture is then passed over a suitable catalyst such as described in U.S. Pat. No. 1,931,858; Brit. Pat. No. 345,253; Ger. Pat. No. 525,836; and M. Cabanac, Compt. rend., 190, 881 (1930), and the vinyl ethyl ether is removed from the off gases. The liberated ethanol is recycled to the reactor.

I claim:

1. A process for producing unsaturated esters by contacting a substantially anhydrous gas mixture comprising (1) an alkene selected from the group consisting of ethylene, propylene, alpha butylene, beta butylene, pentene, cyclohexene and styrene; (2) oxygen, and (3) an alkanoic acid having 1 to about 5 carbon atoms, with a Group VIII noble metal compound and a redox component therefor supported on a solid support, in the presence of a member selected from the group consisting of alkali metal and alkaline earth metal salts of said alkanoic acid; under conditions sufficient to convert said alkene, oxygen and acid to said unsaturated ester.

2. The method of claim 1 wherein said alkene, acid, oxygen and salt are converted to said ester in the presence of a compound of platinum or palladium, said alkene is ethylene, said alkanoic acid is acetic acid, and said salt is selected from alkali metal and alkaline earth metal acetates.

3. The method of claim 2 wherein said salt is supported on said solid support, and said support comprises silica.

4. The process of claim 1 wherein at least a portion of said unsaturated ester is hydrolyzed to produce the corresponding carboxylic acid, and said carboxylic acid is recycled as a portion of said substantially anhydrous gas mixture.

5. The method of claim 1 wherein said redox component is a metal compound which may be present in various oxidation stages under the reaction conditions and said Group VIII metal compound is a palladium compound.

6. The method of claim 5 wherein said metal compound is selected from compounds of copper, mercury, lead, cerium, thallium, tin, titanium, vanadium, antimony, chromium, molybdenum, uranium, manganese, nickel, iron, and cobalt.

7. The process of preparing vinyl acetate which comprises contacting a vaporous mixture comprising (1) ethylene, (2) an oxygen-containing gas, and (3) acetic acid, with a platinum or palladium compound and a redox component therefor, said compound and said redox component being supported on a solid support, in the presence of a member selected from the group consisting of alkali metal and alkaline earth metal salts of acetic acid, under conditions sufficient to convert said ethylene, oxygen, and acetic acid to vinyl acetate.

8. The process of preparing vinyl acetate which comprises a vaporous mixture comprising (1) ethylene, (2) oxygen, and acetic acid with a palladium compound and a redox component therefor, said compound and said redox component being supported on a solid support, in the presence of a member selected from the group consisting of alkali metal and alkaline earth metal salts of acetic acid under conditions sufficient to convert said ethylene, oxygen and acetic acid to said vinyl acetate.

9. A vapor phase process for the preparation of unsaturated esters which comprises passing a substantially anhydrous gas mixture comprising (1) an unsaturated organic compound selected from the group consisting of alkenes and styrene, (2) a carboxylic acid having the formula R'COOH wherein R' is selected from the group consisting of alkyl, aralkyl, aryl and carboxy derivatives thereof having from 1 to 17 carbon atoms per molecule, and (3) oxygen, over a Group VIII noble metal compound and a redox agent therefor, said noble metal compound and said redox agent being supported on a solid support, said gas mixture being contacted with said supported noble metal compound and redox agent in the presence of a member selected from the group consisting of alkali metal and alkaline earth metal salts of said alkanoic acid 10. The process in accordance with claim 9 wherein said noble metal compound comprises compounds of platinum or palladium.

11. The method of claim 7 wherein said ethylene, oxygen-containing gas and acetic acid are contacted in the presence of an alkali metal salt of acetic acid, a palladium compound and a redox component selected from metal compounds which may be present in various oxidation stages under the reaction conditions.

* * * * *